(12) United States Patent
Belanger et al.

(10) Patent No.: US 10,060,560 B2
(45) Date of Patent: Aug. 28, 2018

(54) HIGH PRESSURE FITTING FOR SUPERCRITICAL FLUID CHROMATOGRAPHY

(71) Applicant: Waters Technologies Corporation, Milford, MA (US)

(72) Inventors: Jonathan L. Belanger, Whitensville, MA (US); Sylvain Cormier, Mendon, MA (US); Steven D. Trudeau, Webster, MA (US); Paul Keenan, Harrisville, RI (US); Daniel J. McCormick, Westford, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 627 days.

(21) Appl. No.: 14/414,138

(22) PCT Filed: Jun. 25, 2013

(86) PCT No.: PCT/US2013/047460
§ 371 (c)(1),
(2) Date: Jan. 12, 2015

(87) PCT Pub. No.: WO2014/014622
PCT Pub. Date: Jan. 23, 2014

(65) Prior Publication Data
US 2015/0211663 A1      Jul. 30, 2015

Related U.S. Application Data

(60) Provisional application No. 61/672,371, filed on Jul. 17, 2012.

(51) Int. Cl.
*F16L 15/04*          (2006.01)
*F16J 15/08*          (2006.01)
(Continued)

(52) U.S. Cl.
CPC .............. *F16L 15/04* (2013.01); *B01D 15/10* (2013.01); *B01D 15/22* (2013.01); *B01D 15/40* (2013.01);
(Continued)

(58) Field of Classification Search
CPC ........ B01D 15/22; B01D 15/40; B01D 15/10; B01J 20/283; G01N 30/603;
(Continued)

(56) References Cited

U.S. PATENT DOCUMENTS 3,440,864 A * 4/1969 Blume ................... G01N 30/56
                                                              210/198.2
4,283,280 A * 8/1981 Brownlee .......... G01N 30/6026
                                                              210/198.2
(Continued)

FOREIGN PATENT DOCUMENTS

GB          2482175        1/2012
WO       2006055675 A1     5/2006
(Continued)

OTHER PUBLICATIONS

International Search Report & Written Opinion in counterpart international patent application No. PCT/US13/47460, dated Nov. 12, 2013; 9 pages.
(Continued)

*Primary Examiner* — David C Mellon
*Assistant Examiner* — Benjamin L Lebron
(74) *Attorney, Agent, or Firm* — Schmeiser, Olsen & Watts LLP; William G. Guerin

(57) ABSTRACT

Described is a mobile phase fitting having reduced corrosion and erosion. The fitting includes a coupling body, compression screw, compression member and gasket. The coupling body has a threaded bore at one end, a tapered cavity, a narrow bore and a fluid channel. The compression screw has
(Continued)

an axial bore to receive a tube and a threaded outer surface in engagement with the threaded bore of the coupling body. The compression member is disposed in the tapered cavity and has an axial opening to pass the tube and a tapered surface to engage a surface of the tapered cavity. The gasket is disposed in the narrow bore and has one surface in contact with the first internal surface and has a parallel surface to receive an end face of the tube. Mobile phase flows along a path that includes the tube, an opening in the gasket and the fluid channel.

13 Claims, 5 Drawing Sheets

(51) Int. Cl.
F16J 15/10 (2006.01)
G01N 30/60 (2006.01)
B01D 15/10 (2006.01)
B01D 15/22 (2006.01)
B01D 15/40 (2006.01)
F16L 19/02 (2006.01)

(52) U.S. Cl.
CPC ......... F16J 15/0806 (2013.01); F16J 15/102 (2013.01); F16L 19/0212 (2013.01); G01N 30/60 (2013.01); G01N 30/6004 (2013.01); G01N 30/6026 (2013.01)

(58) Field of Classification Search
CPC ........... G01N 30/6026; G01N 30/6004; G01N 2030/085; G01N 2030/328; G01N 30/60; F16L 15/04; F16L 19/062; F16L 29/02; F16L 19/0212; F16J 15/0806; F16J 15/102; F16K 15/04
See application file for complete search history.

(56) References Cited

U.S. PATENT DOCUMENTS

| | | | | |
|---|---|---|---|---|
| 4,451,363 | A * | 5/1984 | Brownlee | B01D 15/22 210/198.2 |
| 4,863,592 | A * | 9/1989 | Allington | B01D 15/08 210/198.2 |
| 5,227,059 | A * | 7/1993 | Shepherd | G01N 30/6004 210/198.2 |
| 7,384,457 | B2 | 6/2008 | Emmons et al. | |
| 8,006,367 | B1 * | 8/2011 | Best | B01L 3/563 29/516 |
| 9,562,879 | B2 * | 2/2017 | Hirmer | F16L 9/147 |
| 2005/0011835 | A1 | 1/2005 | Henderson et al. | |
| 2005/0082213 | A1 * | 4/2005 | DeMarco | B01D 15/22 210/198.2 |
| 2005/0152820 | A1 | 7/2005 | D'Evelyn et al. | |
| 2006/0151998 | A1 * | 7/2006 | Dourdeville | F16L 13/103 285/285.1 |
| 2010/0018928 | A1 * | 1/2010 | Charlton | B01D 15/22 210/661 |
| 2011/0259827 | A1 | 10/2011 | Belanger et al. | |
| 2012/0061955 | A1 | 3/2012 | Hochgraeber et al. | |
| 2012/0228872 | A1 | 9/2012 | Gamache et al. | |

FOREIGN PATENT DOCUMENTS

| | | |
|---|---|---|
| WO | 2012177403 | 12/2012 |
| WO | 2013134087 | 9/2013 |

OTHER PUBLICATIONS

International Preliminary Report on Patentability in international patent application No. PCT/US13/47460, dated Jan. 29, 2015; 8 pages.
Extended European Search Report in counterpart European Patent Application No. 13820229.6, dated Apr. 26, 2016; 12 pages.

* cited by examiner

HIGH PRESSURE FITTING FOR SUPERCRITICAL FLUID CHROMATOGRAPHY

RELATED APPLICATION

This application claims the benefit of the earlier filing date of U.S. Provisional Patent Application Ser. No. 61/672,371, filed Jul. 17, 2012 and titled "High Pressure Fitting for Supercritical Fluid Chromatography," the entirety of which is incorporated herein by reference.

FIELD OF THE INVENTION

The invention relates generally to couplings for chromatography systems. More particularly, the invention relates to a high pressure fitting to reduce corrosion and erosion at couplings in supercritical fluid chromatography systems.

BACKGROUND

Supercritical fluid chromatography (SFC) is a type of normal phase chromatography that typically uses carbon dioxide as the mobile phase. SFC combines many of the features of liquid chromatography (LC) and gas chromatography (GC), and can often be used for separations with compounds that are not suitable for LC or GC. For example, SFC chromatography can be advantageous for separation and analysis of hydrophilic and chiral compounds, lipids, thermally-labile compounds and polymers. Other advantages include the lower cost and toxicity of the mobile phase compared to many liquid mobile phases and carrier gases.

The carbon dioxide mobile phase is generally at a pressure and temperature where the mobile phase remains in a supercritical fluid state. More specifically, the carbon dioxide mobile phase is in a supercritical fluid state at a temperature greater than 31° C. and pressure greater than 73 atm. Typically the mobile phase also includes a solvent additive. A common solvent additive is methanol. Examples of other solvent additives include acetonitrile and alcohols such as ethanol and isopropanol.

The SFC mobile phase path can exhibit problems that are generally not observed with LC and GC systems. In particular, corrosion and erosion can occur at various fluid connections in the chromatography system such as at the injector couplings and at the entrance and exit couplings of the column. For example, a mobile phase tube can internally erode near the exit end of the tube over time so that the inner diameter increases to leave an eroded region having a funnel shape at the end face of the tube. Moreover, the end faces of the tubing and surfaces of mating ports can corrode and exhibit pitting. Other locations in the system that may experience corrosion or erosion include dead volumes or regions of expanding volume. The effects of the corrosion and erosion may include the loss of pressure, loss of flow, or phase change, which affect retention times. Other negative effects may include carryover, bandspreading and changes in the shape of chromatogram peaks.

SUMMARY

In one aspect, the invention features a mobile phase fitting that includes a coupling body, a compression screw, a compression member and a gasket. The coupling body has a first threaded bore at a first end, a tapered cavity, a narrow bore and a fluid channel. The tapered cavity extends from an internal end of the threaded bore. The narrow bore extends from an end of the tapered cavity that is opposite to the threaded bore to a first internal surface. The fluid channel extends from the first internal surface to a second internal surface. The compression screw has an axial bore to receive a tube for passing a mobile phase and also has a threaded outer surface in engagement with the threaded bore of the coupling body. The compression member is disposed within the tapered cavity and has an axial opening to pass the tube and a tapered surface to engage a surface of the tapered cavity. The gasket is disposed in the narrow bore and has a pair of parallel surfaces with an opening therebetween. One of the parallel surfaces is in contact with the first internal surface and the other parallel surface is configured to receive an end face of the tube. The mobile phase flows along a path that includes the tube, the opening in the gasket and the fluid channel of the coupling body.

In another aspect, the invention features a mobile phase fitting that includes a coupling body, a compression screw, a compression member, a tube and a gasket. The coupling body has a first threaded bore at a first end, a tapered cavity, a narrow bore and a fluid channel. The tapered cavity extends from an internal end of the threaded bore. The narrow bore extends from an end of the tapered cavity that is opposite to the threaded bore to a first internal surface. The fluid channel extends from the first internal surface to a second internal surface. The compression screw has an axial bore and a threaded outer surface in engagement with the threaded bore of the coupling body. The compression member is disposed within the tapered cavity and has an axial opening and a tapered surface to engage a surface of the tapered cavity. The tube has an end face and extends through the axial bore of the compression screw and the axial opening of the compression member. The gasket has a pair of parallel surfaces with an opening therebetween is secured to the end of the tube. One of the parallel surfaces is in contact with the end face of the tube and the other of the parallel surfaces is in contact with the first internal surface. The mobile phase flows along a path that includes the tube, the opening in the gasket and the fluid channel of the coupling body.

In yet another aspect, the invention features a SFC column assembly that includes a SFC column, a pair of coupling nuts and a pair of gaskets. Each coupling nut is secured at one end to an end of the SFC column and has a threaded bore for receiving a compression screw at an opposite end. Each coupling nut has a narrow bore to receive a tube for conducting a supercritical fluid, a tapered cavity to receive a compression member and a fluid channel. The tapered cavity extends from an internal end of the threaded bore. The narrow bore extends from an end of the tapered cavity that is opposite to the threaded bore to a first internal surface. The fluid channel extends from the first internal surface to a second internal surface. Each gasket is disposed in the narrow bore of a respective one of the coupling nuts and has a pair of parallel surfaces with an opening therebetween. One of the parallel surfaces is in contact with the first internal surface of the coupling nut and the other parallel surface is configured to receive an end face of one of the tubes.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

SFC systems typically employ a carbon dioxide mobile phase at a pressure and temperature sufficient to maintain the mobile phase in a supercritical fluid state. Often the mobile phase further includes methanol or another solvent modifier. The presence of the solvent modifier significantly increases corrosion and erosion that occur at various fluid connections, such as where tubing that carries the mobile phase is coupled to a SFC system component. Fluid connections at the ends of the SFC column and at fittings, such as at the injector, can experience pitting and erosion after just a few weeks of operation. If a small leak occurs at a fitting, the corrosion process is accelerated and can affect chromatographic measurements after as little as one week. Other locations within the SFC system that can exhibit corrosion and erosion include regions where the carbon dioxide mobile phase undergoes a phase change, dead volumes and regions of expanding volume along the mobile phase path.

In brief overview, the invention relates to a mobile phase fitting that includes a coupling body, a compression screw, a compression member and a gasket, for example, as described below in various embodiments. In some embodiments, the mobile phase fitting is part of a SFC system. Advantageously, the mobile phase fitting reduces or eliminates corrosion and erosion at the fluid connection and therefore reduces or eliminates the degradation of chromatographic data acquired by the SFC system.

Figure 1A:
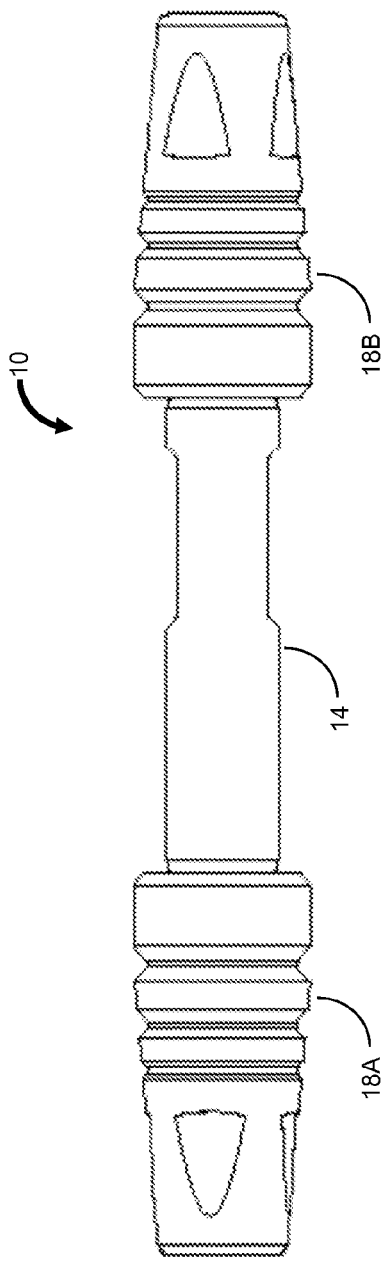
FIG. 1A is a side view of a SFC column assembly for a SFC system.
Figure 1B:
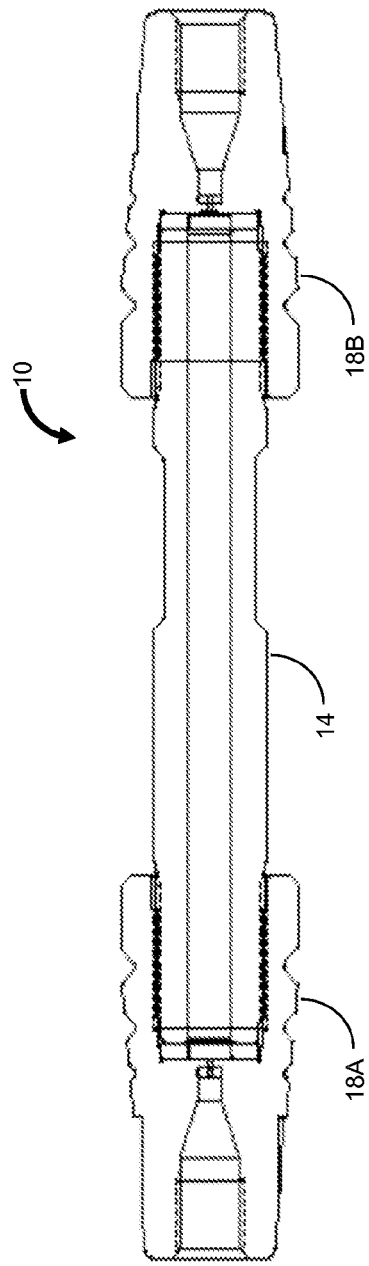
FIG. 1B is a cross-sectional side view of a SFC column assembly for a SFC system.

FIG. 1A and FIG. 1B show a side view and a cross-sectional side view, respectively, of a SFC column assembly 10 for a SFC system. The assembly 10 includes a SFC column 14 and two coupling bodies shown in the illustrations as end nuts 18.

As used herein, a SFC column means any chromatography column that is suitable for performing SFC separations. A typical SFC column includes a stationary phase packed in a structure that is configured to receive a supercritical mobile phase at one end and to provide the supercritical mobile phase at an opposite end. For example, the structure can be substantially cylindrically-shaped with an axial bore that is packed with the stationary phase. For typical separations, compounds in the mobile phase that leaves the SFC column are separated according to their retention times.

Figure 2A:
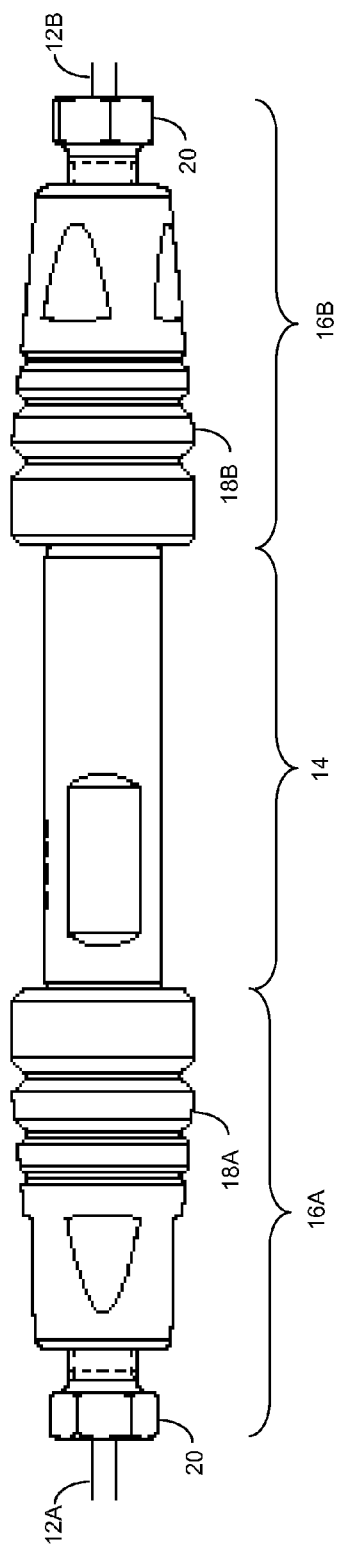
FIG. 2A is an illustration of the SFC column assembly of FIG. 1A coupled into a mobile phase path of a SFC system.

FIG. 2A shows the SFC column assembly 10 of FIG. 1A coupled into a mobile phase path. Stainless steel tubing 12A provides the mobile phase and sample to the SFC column 14 and is connected at one end by a fitting 16A. Additional tubing 12B conducts the eluent from the SFC column 14 and is connected at the opposite end by another fitting 16B. Each fitting 16 includes a coupling body, a compression screw 20, a compression member and a gasket to secure the tubing 12 to the column 14 to achieve a fluid-tight seal. Preferably, the coupling body (shown in the form of an end nut 18), compression screw 20 and compression member are constructed of stainless steel.

Figure 2B:
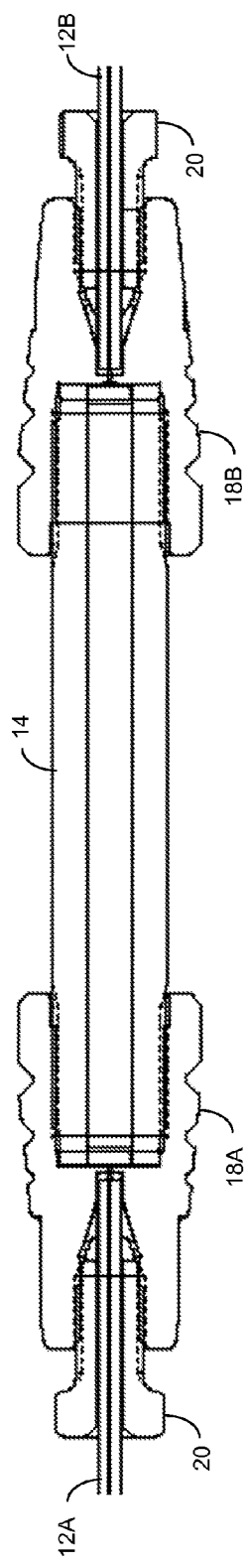
FIG. 2B is an illustration of the SFC column assembly of FIG. 1B coupled into a mobile phase path of a SFC system.

FIG. 2B shows the SFC column assembly 10 of FIG. 1B coupled into the mobile phase path by tubing 12 which passes through the compression screws 20. The tubing 12A is coupled to one end nut 18A so that supercritical fluid exiting at the end face of the tubing 12A passes through a fluid channel and into one end of the SFC column 14. The supercritical fluid exiting the other end of the SFC column 14 flows through a similar fluid channel in the other end nut 18B and into tubing 12B which conducts the supercritical fluid to a detection system (not shown). The detection system is configured to determine the presence and/or amounts of one or more compounds in a sample injected into the mobile phase.

Figure 3A:
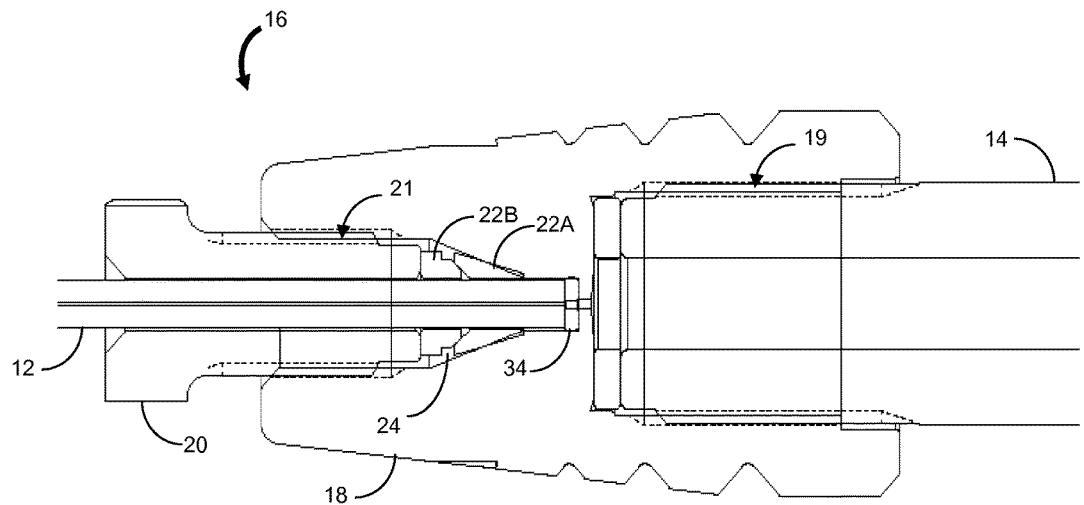
FIG. 3A is a detailed cross-sectional view of one of the fittings shown in FIG. 2B.
Figure 3B:
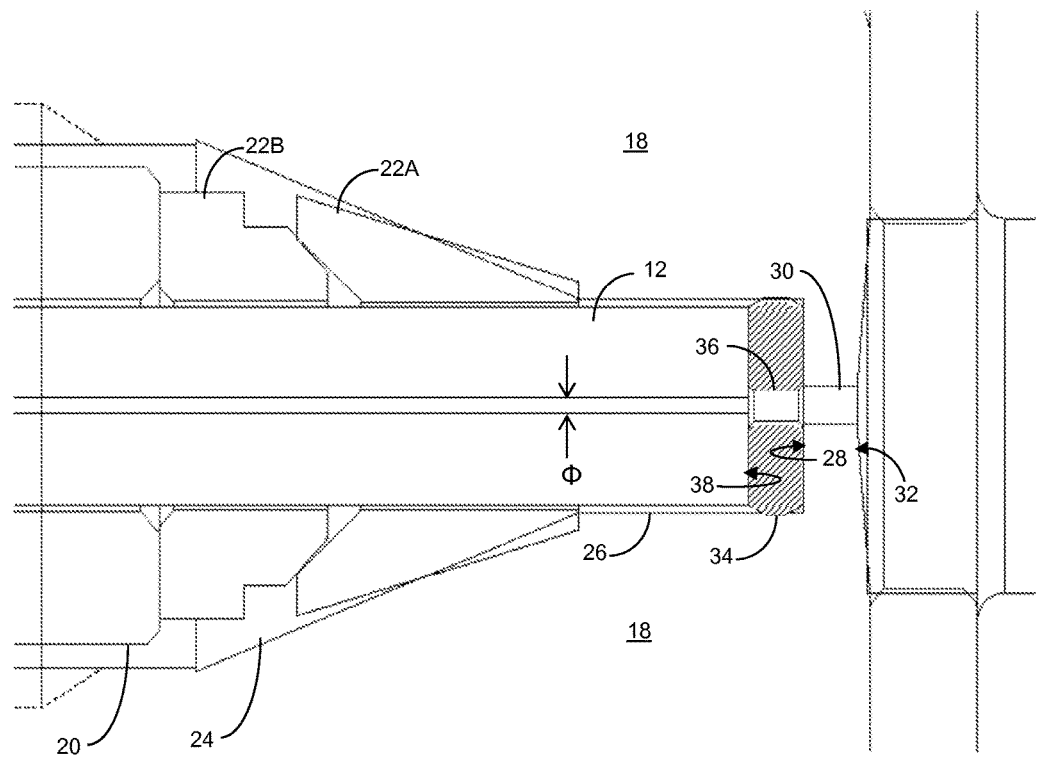
FIG. 3B is a magnified cross-sectional view of a portion of the coupling nut and other fitting elements for the fitting shown in FIG. 3A.

FIG. 3A is a detailed cross-sectional view of one of the fittings 16 in the region where the mobile phase flows into or out from the SFC column 14. FIG. 3B is a magnified view of a portion of the end nut 18 and other fitting elements from FIG. 3A, and shows how the fitting 16 provides a fluidic seal between the tubing 12 and the SFC column 14.

A threaded bore at one end of the end nut 18 allows it to be secured in a threaded region 19 to a threaded surface of the SFC column 14. A second threaded bore at the opposite end of the end nut 18 receives the threaded surface of a compression screw 20 in another threaded region 21. The tubing 12 passes through an axial bore in the compression screw 20, through an axial opening in a compression member 22 in a tapered cavity 24 and into a narrow bore 26 of the end nut 18. By way of example, the tubing 12 can be stainless steel tubing having an inner diameter φ of 0.005 in. The narrow bore 26 extends axially from the tapered cavity 24 to a first internal surface 28 and a fluid channel 30 extends from the first internal surface 28 to a second internal surface 32 which in the illustrated embodiment is a conical surface that expands from the diameter of the fluid channel 30 to the inner diameter of the SFC column 14.

A gasket 34 having a central opening 36 is positioned inside the narrow bore 26 and against the first internal surface 28. In one embodiment the gasket 34 is secured in place by an interference fit between the outer circumference of the gasket 34 and the circumference of the narrow bore 26. The gasket 34 acts as a face seal against the end face 38 of the tubing 12 and substantially prevents any leakage along the fluid path between the end face 38 and the fluid channel 30.

During installation of the fitting, the compression screw 20 is rotated so that the compression member 22 is urged into the tapered cavity 24 until a tapered surface of the compression member 22 engages the internal end nut surface that surrounds the tapered cavity 24. In the illustrated embodiment, the compression member 22 includes a forward ferrule 22A that engages the internal surface and a back ferrule 22B. When installation is complete, the load applied by the compression screw 20 maintains the end face 38 of the tubing 12 against the flat surface of the gasket 34 that is opposite to the first internal surface 28 to thereby achieve a fluidic seal. Thus a supercritical fluid passes from tubing 12A through the fitting to the SFC column 14 or from the SFC column 14 to tubing 12B without coming into contact with the first internal surface 28. Consequently, corrosion and erosion of the first internal surface 28, which can lead to microleaks and degradation of chromatographic performance, are substantially reduced or eliminated.

The gasket material is selected for its resistance to the corrosion and erosion effects of the supercritical fluid. In a preferred embodiment the gasket 34 is formed in a polymer material. By way of a specific example, the polymer material can be VESPEL® (available from DuPont Vespel™ of Newark, Del.). Other gasket materials may be used. For example, the gasket 34 may be fabricated from gold which has high malleability, resistance to corrosion and is significantly chemically inert. An example of another corrosion-resistant, relatively chemically inert material for the gasket 34 is tantalum. In another embodiment the gasket 34 is a metal gasket that includes a gold or tantalum coating. In these embodiments the supercritical fluid does not come into contact with the first internal surface 28 of the end nut 18 thus the internal corrosion that occurs in conventional fittings after extended use is substantially reduced or eliminated.

In some applications the gold-coated metal gasket may be preferred over a polymer gasket. For example, the lifetime of a consumable SFC column may be substantially less than the time for the gold coating to erode and expose the underlying metal. In addition, the cost of a SFC column assembly having fittings with gold coated metal gaskets may be less for some applications than the cost of a SFC column assembly having fittings with polymer gaskets.

Figure 4:
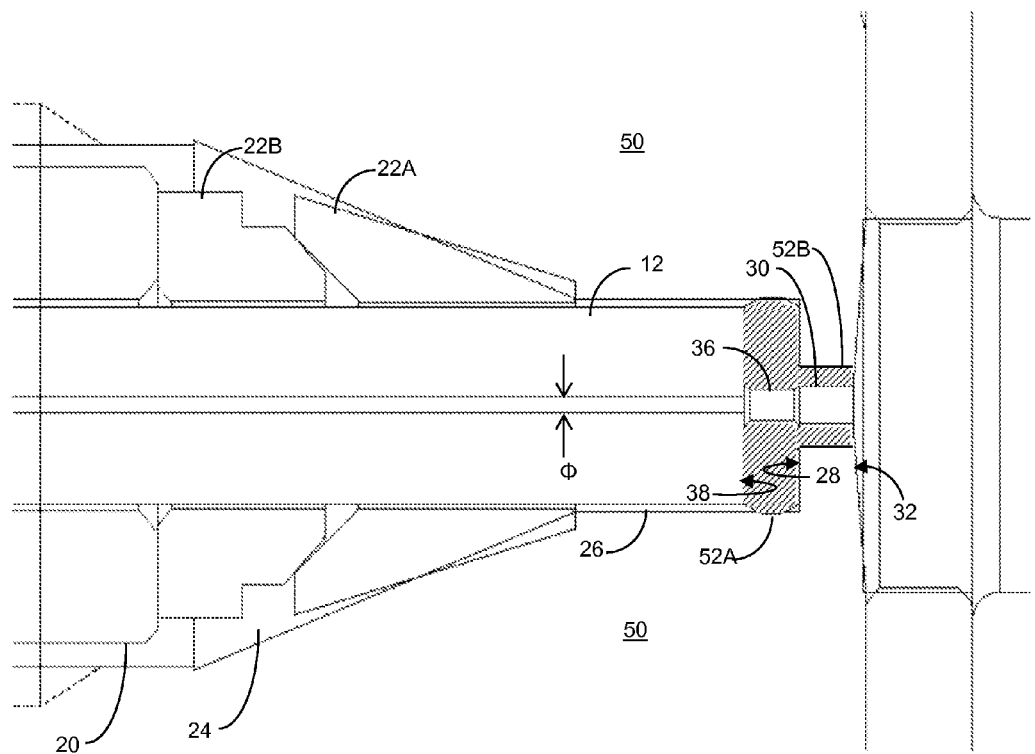
FIG. 4 is a magnified cross-sectional view of a portion of a coupling nut and other fitting elements for another embodiment of a fitting according to the invention.

FIG. 4 shows a magnified view of a portion of an end nut 50 and other fitting elements according to another embodiment of a fitting. In the illustrated embodiment, the supercritical fluid exiting at the end face 38 of the tubing 12 does not come into contact with the first internal surface 28 and the circumference of the fluid channel 30. The gasket 52 includes a body portion 52A and a stem portion 52B. The body portion 52A is located against the first internal surface 28 with the stem portion 52B extending from the body portion 52A through the fluid channel 30 and to the second internal surface 32. An axial gasket opening (or passage) extends from the surface of the body portion 52A that is against the end face 38 and through the full length of the stem portion 52B. The outer diameter of the stem portion 52B is approximately equal to the diameter of the fluid channel 30 to achieve an interference fit. Alternatively, or in addition, the outer diameter of the body portion 52A is approximately equal to the inner diameter of the narrow bore 26 to achieve an interference fit.

The embodiments described above include a gasket 34 or 52 in the narrow bore 26 and adjacent to the first internal surface 28. Alternatively, the gasket may be omitted and certain internal portions of the fitting may be gold coated. For example, a coating, such as gold or tantalum, can be applied to one or more of the circumference of the fluid channel 30, the circumference of the narrow bore 26 and the first internal surface 28. In another example, the coating can be applied to one or more regions of the tubing 12 such as the end face 38 and the portion of the length of the inner and/or outer surfaces of the tubing 12 that lie within the narrow bore 26.

Figure 5:
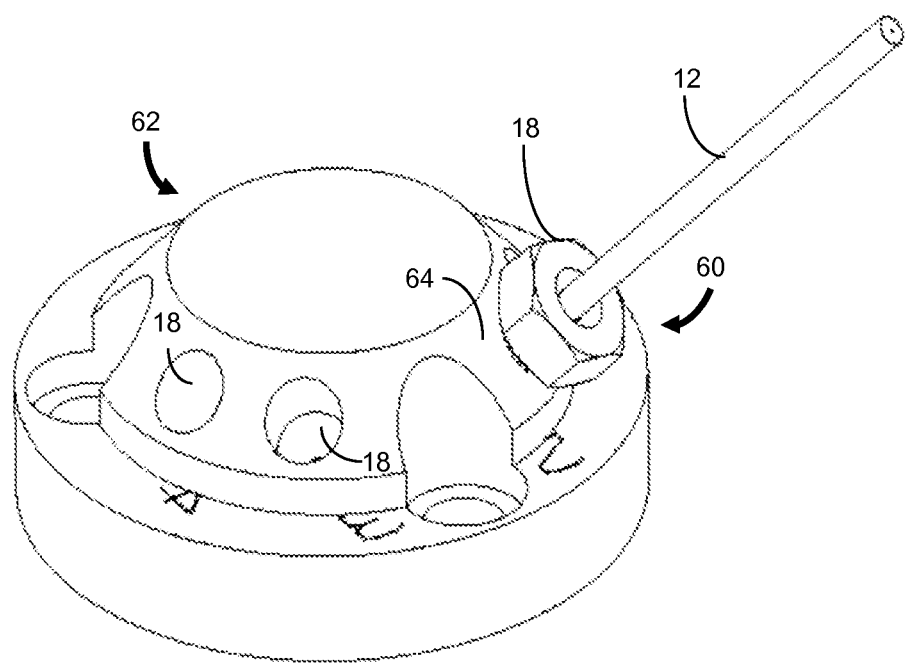
FIG. 5 shows an embodiment of a fitting according to the invention and used for coupling a mobile phase path to a rotary shear seal valve that injects a sample into a mobile phase.

In the embodiments described above, the fittings are used to couple a supercritical mobile phase to or from a SFC column; however, the fittings are suitable for use in other applications such as for coupling a mobile phase to or from other SFC system components. FIG. 5 shows an example of a fitting 60 that couples a stainless steel tubing 12 to a portion (coupling body 64) of a rotary shear seal valve 62 used to inject a sample into a mobile phase. In another example, the fitting can be used to couple stainless steel tubing from the SFC column assembly to the inlet of a flow cell detector.

While the invention has been shown and described with reference to specific embodiments, it should be understood by those skilled in the art that various changes in form and detail may be made therein without departing from the spirit and scope of the invention as recited in the accompanying claims. For example, although described above relate primarily to SFC system applications, it will be recognized that in various embodiments the fittings can be suitable for use in other chromatography systems such as high performance liquid chromatography (HPLC) and ultra performance liquid chromatography (UPLC). One advantage for such systems is the elimination of microleaks which can otherwise occupy unswept regions and adversely affect chromatographic data.

What is claimed is:

1. A mobile phase fitting, comprising:
   a coupling body having a first threaded bore at a first end, a tapered cavity, a narrow bore and a fluid channel, the tapered cavity extending from an internal end of the first threaded bore, the narrow bore extending from an end of the tapered cavity that is opposite to the first threaded bore to a first internal surface, the fluid channel extending from the first internal surface to a second internal surface;
   a compression screw having an axial bore to receive a tube for passing a mobile phase and a threaded outer surface in engagement with the first threaded bore of the coupling body;
   a compression member disposed within the tapered cavity and having an axial opening to pass the tube and a tapered surface to engage a surface of the tapered cavity; and
   a gasket disposed in the narrow bore and having a pair of parallel surfaces and a stem portion, one of the parallel surfaces in contact with the first internal surface and the other parallel surface configured to receive an end face of the tube, the stem portion having a length that extends from the first internal surface to the second internal surface, wherein the gasket has an opening that extends between the parallel surfaces and through the length of the stem portion, and wherein the mobile phase flows along a path that includes the tube, the opening in the gasket and the fluid channel of the coupling body such that the mobile phase does not contact the first internal surface and does not contact a circumference of the fluid channel of the coupling body.

2. The mobile phase fitting of claim 1 wherein the coupling body has a second end opposite to the first end and wherein the coupling body has a second threaded bore extending from the second end to the second internal surface.

3. The mobile phase fitting of claim 2 wherein the second threaded bore of the coupling body is configured to engage a threaded surface of a chromatography system component.

4. The mobile phase fitting of claim 3 wherein the chromatography system component is a chromatography column.

5. The mobile phase fitting of claim 1 wherein the mobile phase is a supercritical fluid.

6. The mobile phase fitting of claim 1 wherein the gasket comprises a polymer material.

7. The mobile phase fitting of claim 1 wherein the compression member comprises at least one ferrule.

8. A mobile phase fitting, comprising:
   a coupling body having a first threaded bore at a first end, a second threaded bore at a second end that is opposite to the first end, a tapered cavity, a narrow bore and a fluid channel, the tapered cavity extending from an internal end of the first threaded bore, the narrow bore extending from an end of the tapered cavity that is opposite to the first threaded bore to a first internal surface, the fluid channel extending from the first internal surface to a second internal surface, the second threaded bore extending from the second end and terminating at the second internal surface;
   a compression screw having an axial bore to receive a tube for passing a mobile phase and a threaded outer surface in engagement with the first threaded bore of the coupling body;
   a compression member disposed within the tapered cavity and having an axial opening to pass the tube and a tapered surface to engage a surface of the tapered cavity; and
   a gasket disposed in the narrow bore and having a pair of parallel surfaces and a stem portion, one of the parallel surfaces in contact with the first internal surface and the other parallel surface configured to receive an end face of the tube, the stem portion having a length that extends from the first internal surface into the fluid channel, wherein the gasket has an opening that extends between the parallel surfaces and through the length of the stem portion, and wherein the mobile phase flows along a path that includes the tube, the opening in the gasket and the fluid channel of the coupling body.

9. The mobile phase fitting of claim 8 wherein the second threaded bore of the coupling body is configured to engage a threaded surface of a chromatography system component.

10. The mobile phase fitting of claim 9 wherein the chromatography system component is a chromatography column.

11. The mobile phase fitting of claim 8 wherein the mobile phase is a supercritical fluid.

12. The mobile phase fitting of claim 8 wherein the gasket comprises a polymer material.

13. The mobile phase fitting of claim 8 wherein the compression member comprises at least one ferrule.

\* \* \* \* \*